United States Patent [19]

Kao

[11] Patent Number: 5,262,423
[45] Date of Patent: Nov. 16, 1993

[54] RAPAMYCIN ARYLCARBONYL AND ALKOXYCARBONYL CARBAMATES AS IMMUNOSUPPRESSIVE AND ANTIFUNGAL AGENTS

[75] Inventor: Wenling Kao, Paoli, Pa.

[73] Assignee: American Home Products Corporation, New York, N.Y.

[21] Appl. No.: 968,115

[22] Filed: Oct. 29, 1992

[51] Int. Cl.$^5$ ............... C07D 498/16; A61K 31/395
[52] U.S. Cl. ................................... 514/291; 540/456
[58] Field of Search ............... 540/456, 454; 546/90; 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rahkit | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,899 | 3/1992 | Calne | 514/291 |
| 5,118,677 | 6/1992 | Caufield | 540/546 |
| 5,118,678 | 6/1992 | Kao et al. | 514/183 |

FOREIGN PATENT DOCUMENTS

WO91/13899 3/1991 PCT Int'l Appl. .

OTHER PUBLICATIONS

Martel, et al., Can. J. Physiol. Pharm. 55, 48∝51, (1977).
Calne, et al., The Lancet, Jun. 3, 1978; pp.
Dumont et al., FASEB 3(4), 5256 (1989).
Staruch et al., FASEB 3(3), 3411 (1989).
Vezina et al., Journal of Antibiotics 28(10), 721-26 (1975).
Sehgal et al., Journal of Antibiotics 28(10), 727-32 (1975).
Baker et al., Journal of Antibiotics 31(6), 539-545 (1978).

*Primary Examiner*—Mukund J. Shah
*Assistant Examiner*—Pavanaram K. Sripada
*Attorney, Agent, or Firm*—R. F. Boswell, Jr.

[57] ABSTRACT

N-arylcarbonyl and N-alkylcarbonyl carbamates of rapamycin of the formula shown below wherein

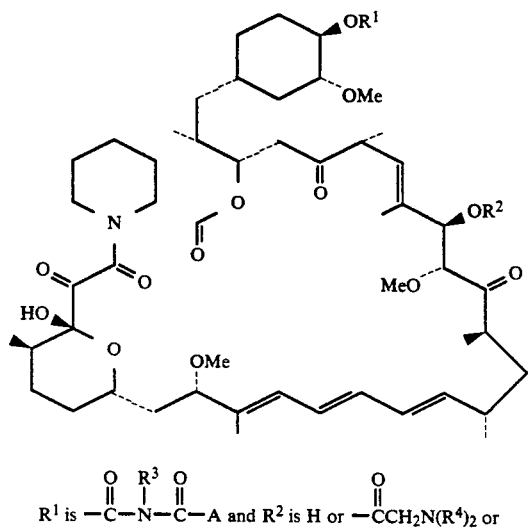

$R^1$ is $-\overset{O}{\underset{\|}{C}}-\overset{R^3}{\underset{|}{N}}-\overset{O}{\underset{\|}{C}}-A$ and $R^2$ is H or $-\overset{O}{\underset{\|}{C}}CH_2N(R^4)_2$ or $R^1$ and $R^2$ are both

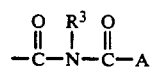

and where A is lower alkoxy or aryl or heteroaryl, $R^3$ is H or methyl and $R^4$ is $C_1$-$C_6$ alkyl, $C_2$-$C_6$ alkenyl or $C_2$-$C_6$ alkynyl possess immunosuppressive and/or antifungal and/or antitumor and/or antiinflammatory activity in vitro and/or inhibit thymocyte proliferation in vivo. These compounds are thus expected to be useful in the treatment of transplantation rejection, autoimmune diseases, fungal infections, cancer, and diseases of inflammation.

9 Claims, No Drawings

RAPAMYCIN ARYLCARBONYL AND ALKOXYCARBONYL CARBAMATES AS IMMUNOSUPPRESSIVE AND ANTIFUNGAL AGENTS

FIELD OF INVENTION

This invention relates to N-arylcarbonyl and N-alkoxycarbonyl carbamates of rapamycin which possess immunosuppressive and/or antifungal and/or antitumor and/or antiinflammatory activity in vivo and/or inhibit thymocyte proliferation in vitro and are therefore useful in the treatment of transplantation rejection, autoimmune diseases (i.e. lupus erythematosus, rheumatoid arthritis, diabetes mellitus, multiple sclerosis), fungal infections (i.e. *Candida albicans*), cancer, and diseases of inflammation.

BACKGROUND OF THE INVENTION

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. Nos. 3,929,992, and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin has been shown to be effective in inhibiting transplant rejection (U.S. Pat. No. 5,100,899). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

U.S. Pat. No. 5,091,389 discloses antifungal and immunosuppressant activities of a desmethyl analog of rapamycin corresponding to 33-desmethylrapamycin according to the numbering convention used herein.

Mono- and diacylated derivatives of rapamycin (positions 28 and 43) have been shown to be useful as antifungal agents (U.S. Pat. No. 4,316,885) and used to make water soluble prodrugs of rapamycin (U.S. Pat. No. 4,650,803). Recently, the numbering convention of rapamycin has been changed; therefore according to Chemical Abstracts nomenclature, the esters described above would be at the 31- and 42-positions.

BRIEF DESCRIPTION OF THE INVENTION

The novel compounds useful in the methods and pharmaceutical composition of his invention have the structure shown in Formula I below.

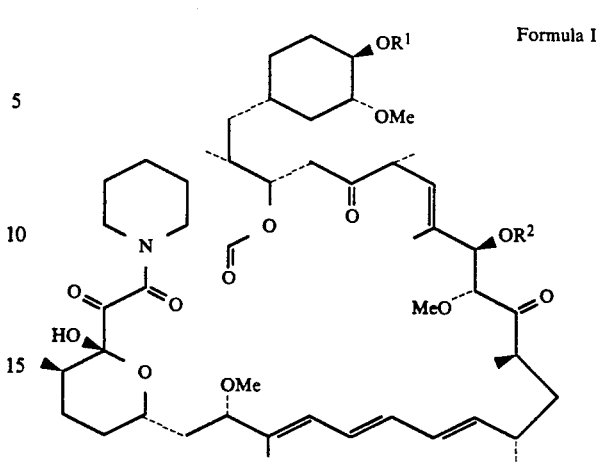

Formula I

Under Formula I,
$R^1$ is

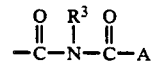

and
$R^2$ is H or

or $R^1$ and $R^2$ are both

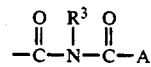

where
$R^3$ is H or methyl, and
A is aryl or heteroaryl of from 6 to 10 atoms, arylalkyl of 7 to 12 atoms, cycloalkyl of from 5 to 8 carbons, alkyl of from 1-6 carbons, adamantyl, quinuclidinyl, or —$OR^4$ where $R^4$ is $C_1$-$C_6$ alkyl, $C_2$-$C_6$ alkenyl, or $C_2$-$C_6$ alkynyl.

Formula I also encompasses the pharmaceutically acceptable salts. The term pharmaceutically acceptable salts encompasses solvates, hydrates, cationic metal salts and acid addition salts which can be formed from organic and inorganic acids including but not limited to, hydrochloric, sulfuric, phosphoric, hydrobromic, acetic, maleic, fumaric, succinic, citric, sulfamic, pamoic, and tartaric acids when $R^2$ is —$COCH_2N(R^4)_2$ or when A is a nitrogen containing heterocycle.

By way of further definition, aryl or heteroaryl of from 6 to 10 atoms mean phenyl, phenyl substituted by fluorine, chlorine, bromine, iodine, nitro, trifluoromethyl, $C_1$-$C_6$ alkyl, $C_1$-$C_6$ alkoxy or cyano; naphthyl or naphthyl substituted by $C_1$-$C_6$ alkyl, $C_1$-$C_6$ alkoxy, fluorine, chlorine, bromine, or iodine; pyridinyl, pyrimidinyl, pyrazinyl, indolyl, quinolinyl, isoquinolinyl, benzofuranyl, benzopyranyl, benzo[b]thiophenyl, benzimidazolyl, and benzthiazolyl. Arylalkyl of 7 to 12 atoms includes benzyl and naphthylethyl. Cycloalkyl includes cyclopentyl, cyclohexyl, cycloheptyl, and cyclooctyl. $C_1$-$C_6$ alkyl encompasses straight and branched chains and includes methyl, ethyl, propyl, isopropyl, butyl, t-butyl, pentyl and hexyl and one or more hydrogens may be replaced with fluorine, chlorine, bromine, or methoxy. $C_2$–$C_6$ alkenyl includes vinyl, allyl, butenyl, and butadienyl. $C_2$–$C_6$ alkynyl includes acetylenyl and propynyl.

Immunosuppressive activity was evaluated in an in vitro standard pharmacological test procedure to measure lymphocyte proliferation (LAF) and in an in vivo procedure to evaluate the survival time of a pinch skin graft. Antifungal activity was determined against five strains of *Candida albicans*.

DETAILED DESCRIPTION OF THE INVENTION

The rapamycin N-arylcarboyl and N-alkoxycarbonyl carbamates of this invention can be prepared by standard literature procedures as outlined in the reaction Scheme I below where R-OH is rapamycin and the hydroxyl group is that at position 42 and/or 31. The arylcarbonyl and alkoxycarbonyl isocyanates are either commercially available or can be prepared by standard literature procedures as described in *Chemical Reviews*, 72(5), p. 469 (1972).

Scheme I.

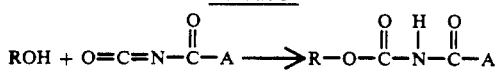

The N-methyl analogs (Scheme 2) may be prepared by procedures analogous to —OH methylation with diazomethane such as the procedure given in Tetrahedron Letters 4405 (1979), N-alkylation and reductive alkylation with formaldehyde and formic acid.

Scheme 2.

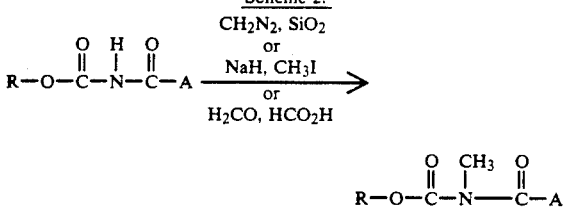

The following specific examples are included for illustrative purposes only and are not to be construed as limiting to this disclosure which is limited only by the scope of the appended claims.

EXAMPLE 1

Rapamycin 42-ester with benzoylcarbamic acid. A solution of 400 mg of rapamycin in a mixture of 2 ml of ether and 8 ml of toluene was treated at 0° C. under nitrogen with 82 mg of benzoyl isocyanate (90%) in one ml of the same. After stirring at 0° C. under nitrogen for 3 hours, the reaction mixture was diluted with 120 ml of ethyl acetate, washed with a saturated sodium bicarbonate solution and brine (2×15 ml). The ethyl acetate solution was dried with magnesium sulfate and evaporated. The residue was chromatographed on silica gel. Elution with ethyl acetate: hexane=1:1 afforded 305 mg of the title product as a white foam.

IR: (KBr) 3440 (OH, NH), 2930, 1775 and 1720 (C=0), 1645 (aromatic) 1450, 1190, 1090 and 990 cm$^{-1}$.

NMR (CDCl$_3$, 400 MHz): δ7.82 (m, 2H, aromatic), 7.58 (m, 1H, aromatic), 7.48 (m, 2H, aromatic), 3.40 (s, 3H, OCH$_3$), 3.33 (s, 3H, OCH$_3$), 3.13 (s, 3H, OCH$_3$).

MS (neg. ion FAB): 1060 (M), 912, 590.

UV: λmax 231.0 (ε,22,938), 267.5 (ε,33,693), 277.0 (ε, 43,378), 288.5 (ε, 32,521) mμ.

EXAMPLE 2

Rapamycin 31-ester with N,N-dimethylglycine, 42-ester with benzoylcarbamic acid. A solution of 300 mg of rapamycin 31-ester with N,N-dimethylglycine (U.S. Pat. No. 4,650,803, Example 1) in 2 ml of dichloromethane was treated at −10° under nitrogen with 73 mg of benzoyl isocyanate (90%) in 2 ml of dichloromethane. After stirring at 0° under nitrogen for three hours, the reaction mixture was diluted with 130 ml of dichloromethane, washed with a saturated sodium bicarbonate and brine. The dichloromethane solution was dried with magnesium sulfate and evaporated. The resulting white foam was dissolved in 0.2 ml of ethyl acetate, diluted with 10 ml of ether and then filtered. The filtrate was cooled to 0° and treated with 0.3 ml of anhydrous 1M HCl in ether. The crystalline salts were collected by filtration, washed with ether and dried at 54° in vacuum to afford 268 mg of the hydrochloride salt monohydrate of the title product as a white solid, mp 124°-128° C.

IR(KBr): 3440 (OH, NH), 2940, 2600–2350

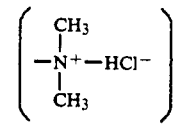

1755 and 1720 (C=0), 1640 (aromatic), 1455, 1095 and 1000 cm$^{-1}$.

NMR (CDCl$_3$, 400 MHz): δ7.84 (d,J=14 cps, 2H, aromatic), 7.50 (m, 1H, aromatic), 7.48 (m, 2H, aromatic). 3.20 (s, 3H, OCH$_3$), 3.04 (s, 3H, OCH$_3$), 2.79 (s, 3H, OCH$_3$).

MS (neg. ion FAB): 1145 (M$^-$), 997.

UV: λmax 233.5 (ε, 23,151), 267.5 (ε,37.354), 277.5 (ε, 48,150), 289.0 (ε, 36,372) μm.

Analysis Calcd. for $C_{63}H_{91}N_3O_{16} \cdot HCl \cdot H_2O$: C, 63.00; H, 7.89; N, 3.49. Found: C, 63.14; H, 7.50; N, 3.86.

EXAMPLE 3

Rapamycin 31,42 diester with benzoylcarbamic acid. A solution of 1.0 g of rapamycin 42-ester with benzoylcarbamic acid in 5 ml of dichloromethane and 5 ml of ether at 0° under nitrogen was treated with 200 mg of benzoyl isocyanate (90%) in 1 ml of dicholormethane. After stirring at 0° under nitrogen for two hours, and at −5° for 18 hours, the reaction mixture was diluted with 180 ml of ethyl acetate. The ethyl acetate solution was washed with a saturated sodium bicarbonate solution, brine, dried with magnesium sulfate and evaporated. The residue was chromatographed on silica gel. Elution with ethyl acetate:hexane=2:3 afforded 70 mg of the title product as a white foam, mp 86°-88°.

IR(KBr): 3450 (OH, NH), 2940, 1770 and 1720 (C=0), 1660 (amide C=0), 1570 (aromatic), 1480, 1190, 1090 and 990 cm$^{-1}$.

NMR (CDCl$_3$, 400 mHz): δ7.78 (m, 2H, aromatic), 7.51 (m, 1H, aromatic), 7.43 (m, 2H, aromatic), 3.36 (s, 3H, OCH$_3$), 3.35 (s, 3H, OCH$_3$), 3.20 (s, 3H, OCH$_3$).

MS (neg. ion FAB): 1207 (M$^-$), 894, 590.

UV: λmax 288.5 (ε, 29,782), 277.0 (ε, 40,689), 267.5 (ε, 3,299) mμ.

EXAMPLE 4

Rapamycin 42-ester with N-methoxycarbonylcarbamic acid. A solution of 300 mg of rapamycin in 2 ml of ethylacetate and 6 ml of ether was treated at −10° under nitrogen with 40 mg of methoxycarbonyl isocyanate (92.5%) in 2 ml of ether. After stirring at 0° under nitrogen for three hours, the reaction mixture was diluted with 180 ml of ethyl acetate washed with a saturated sodium bicarbonate solution and brine. The ethyl acetate solution was dried with magnesium sulfate and evaporated. The residue was chromatographed on silica gel. Elution with ethyl acetate:hexane=2:1 afforded 270 mg of the title product as a white foam, mp 109°-112°.

IR (KBr): 3440 (OH, NH), 2920, 1800

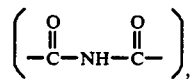, 1725 (C=O), 1635 (C=O amide). 1515, 1450, 1185, 1090, 990 cm$^{-1}$.

NMR (CDCl$_3$, 400 MHz): δ3.79 (s, 3H,

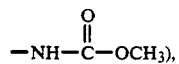, 3.37 (s, 3H, OCH$_3$), 3.33 (s, 3H, OCH$_3$), 3.13 (s, 3H, OCH$_3$).

MS (neg. ion FAB): 1014(M$^-$), 912, 590.

UV: λmax 288.5 (ε, 33,393), 277.0 (ε, 44,038), 267.0 (ε, 33,611) mµ.

Immunosuppressive activity was evaluated in an in vitro standard pharmacological test procedure to measure lymphocyte proliferation (LAF) and in one in vivo standard pharmacological test procedure to evaluate the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cell are cultured with and without various concentrations of rapamycin, cyclosporin A, or test compound. Cells are harvested and incorporated; radiactivity is determined. Inhibition of lymphoproliferation is assessed in percent change in counts per minute from non-drug treated controls. The results are expressed by the following ratio:

$$\frac{{}^3\text{H-control thymus cells} - {}^3\text{H-rapamycin-treated thymus cells}}{{}^3\text{H-control thymus cells} - {}^3\text{H-test compound-treated cells}}$$

or as percent inhibition or IC$_{50}$.

The in vivo test procedure is designed to determine the survival time of pinch skin graft from male BALB/c donors transplanted to male C$_3$H recipients. The method is adapted from Billingham R. E. and Medawar P. B., J. Exp. Biol. 28:385–402, (1951). Briefly, a pinch skin graft from the donor is grafted on the dorsum of the recipient as a allograft, and an isograft is used as control in the same region. The recipients are treated with the test compound, intraperitoneally once daily for 6 consecutive days. Untreated recipients serve as rejection control. The graft is monitored daily and observations are recorded until the graft becomes 95% area necrosis or the suture line is off. This is considered as the rejection day. The graft survival time is one day before the rejection day. The mean graft survival time (number of days ±S.D.) of the drug treatment group is compared with the control group. As transplanted skin grafts are typically rejected within 6–7 days without the use of an immunosuppressant agent, the increased survival time of the skin graft when treated with the compounds of this invention further demonstrate their utility as immunosuppressive agents.

The following table summarizes the results of representative compounds of this invention in these standard test procedures.

TABLE 1

| Compounds | LAF Assay IC$_{50}$ (nM) | | Skin Graft Model (Survival time days) |
|---|---|---|---|
| | Analogs | Rapamycin | |
| Example 1 | 1.4 | 6.7 | 10.5 ± 0.55 |
| Example 2 | 4.8 | 4.2 | 10.4 ± 0.55 |
| Example 3 | 1.20 | 0.83 | — |
| Example 4 | 2.70 | 3.90 | 10.33 ± 0.52 |
| Rapamycin | | | >12.0 |

Based on the results of these standard pharmacological test procedures, the compounds are useful in the treatment of transplantation rejection such as heart, kidney, liver, bone marrow, and skin transplants; autoimmune diseases such as lupus, rheumatoid arthritis, diabetes mellitus, myasthenia gravis, and multiple sclerosis; and diseases of inflammation such as psoriasis, dermatitis, eczema, seborrhea, and inflammatory bowel disease.

Antifungal activity of the compounds of this invention is measured against 5 strains of *Candida albicans* using a plate test procedure for measurement of inhibition. The following represents the typical procedure used. The compound to be tested is placed on sterile dried ¼" plate disks, and allowed to dry. Agar plates are seeded with fungi and allowed to solidify. The impregnated disks are placed on the seeded Agar surface and incubated for the time required for the particular culture. Results shown in Table II are expressed in Minimum Inhibitory Concentration (MIC) (µg/ml) to inhibit growth.

TABLE II

| Compound | Anti-Candida Activity (µg/mL)* | | | | |
|---|---|---|---|---|---|
| | ATCC 10231 | ATCC 38246 | ATCC 38247 | ATCC 38248 | 3669 |
| Example 1 | 0.05 | 0.1 | 0.05 | 0.1 | 0.1 |
| Example 2 | 0.1 | 0.4 | 0.1 | 0.4 | 0.4 |
| Example 4 | .05 | 0.2 | 0.05 | 0.1 | 0.2 |
| Rapamycin | 0.003 | 0.025 | 0.003 | 0.006 | 0.025 |

*Minimal Inhibitory Concentration (MIC)

Pharmaceutical Composition

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixtures with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient: the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-5 percent, preferably 2%, of active compound which may be administered to a fungally affected area.

What is claimed is:

1. A compound according to the formula:

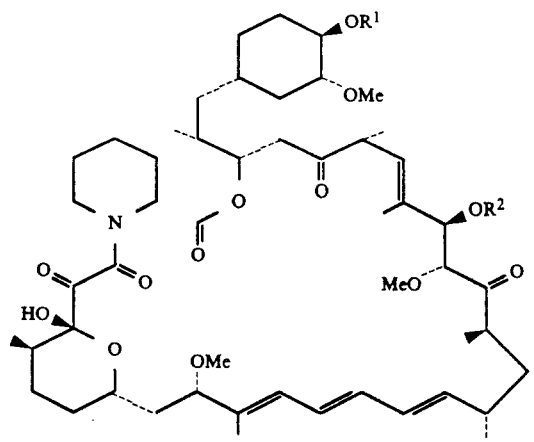

wherein
$R^1$ is

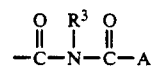

and
$R^2$ is H or

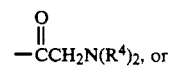

$R^1$ and $R^2$ are both

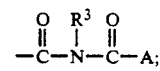

$R^3$ is H or methyl,
A is $-OR^4$ where $R^4$ is $C_1-C_6$ alkyl, $C_2-C_6$ alkenyl, or $C_2-C_6$ alkynyl optionally substituted fluorine, chlorine, bromine, iodine, methoxy or ethoxy; arylalkyl or 7 to 12 atoms, aryl selected from phenyl or phenyl substituted by one or two groups selected from fluorine, chlorine, bromine, iodine, nitro, trifluoromethyl, $C_1-C_6$ alkyl, $C_1-C_6$ alkoxy, cyano; naphthalenyl, naphthalenyl substituted by $C_1-C_6$ alkyl, $C_1-C_6$ alkoxy, fluorine, chlorine, bromine or iodine; heteroaryl selected from pyridinyl, pyrimidinyl, pyrazinyl, indolyl, quinolinyl, isoquinolinyl, benzofuranyl, benzopyranyl, benzo[b]thiophenyl, benzimidazolyl, benzthiazolyl; cycloalkyl selected from cyclopentyl, cyclohexyl, adamantyl; or quinuclidinyl,
or a pharmaceutically acceptable salt thereof.

2. A compound according to claim 1 wherein A is phenyl or methoxy.

3. A compound according to claim 1 which is rapamycin 42-ester with benzoylcarbamic acid.

4. A compound according to claim 1 which is rapamycin 31-ester with N,N-dimethylglycine, 42-ester with benzoylcarbamic acid.

5. A compound according to claim 1 which is rapamycin-31,42-diester with benzoylcarbamic acid.

6. A compound according to claim 1 which is rapamycin 42-ester with N-methoxycarbonylcarbamic acid.

7. A method of treating transplantation rejection, host vs. graft disease, and diseases of inflammation in a mammal by administering thereto an effective amount of a compound having the formula:

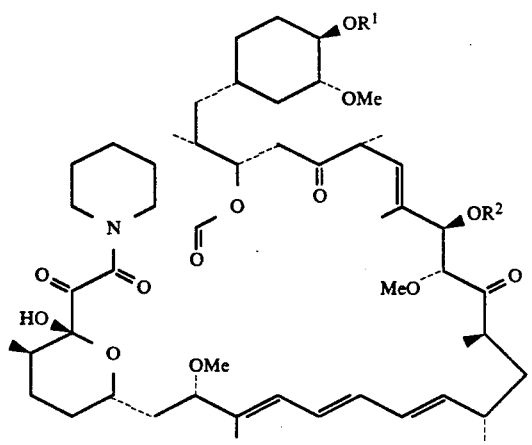

wherein
R¹ is

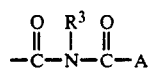

and
R² is H or

R¹ and R² are both

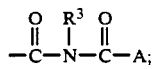

R³ is H or methyl,
A is —OR⁴ where R⁴ is $C_1$–$C_6$ alkyl, $C_2$–$C_6$ alkenyl, or $C_2$–$C_6$ alkynyl optionally substituted fluorine, chlorine, bromine, iodine, methoxy or ethoxy; arylalkyl of 7 to 12 atoms, aryl selected from phenyl or phenyl substituted by one or two groups selected from fluorine, chlorine, bromine, iodine, nitro, trifluoromethyl, $C_1$–$C_6$ alkyl, $C_1$–$C_6$ alkoxy, cyano; naphthalenyl, naphthalenyl substituted by $C_1$–$C_6$ alkyl, $C_1$–$C_6$ alkoxy, fluorine, chlorine, bromine or iodine; heteroaryl selected from pyridinyl, pyrimidinyl, pyrazinyl, indolyl, quinolinyl, isoquinolinyl, benzofuranyl, benzopyranyl, benzothiophenyl, benzimidazolyl, benzthiazolyl; cycloalkyl selected from cyclopentyl, cyclohexyl, adamantyl; or quinuclidinyl,
or a pharmaceutically acceptable salt thereof.

8. A method of treatment according to claim 7 wherein A is phenyl or methoxy.

9. A pharmaceutical composition comprising a pharmaceutical carrier and an effective amount of a compound of the formula:

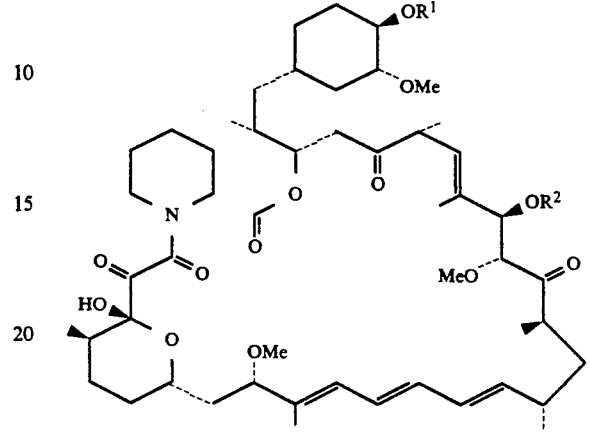

wherein
R¹ is

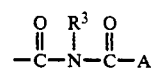

and R² is H or

R¹ and R² are both

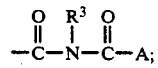

R³ is H or methyl,
A is —OR⁴ where R⁴ is $C_1$–$C_6$ alkyl, $C_2$–$C_6$ alkenyl, or $C_2$–$C_6$ alkynyl optionally substituted fluorine, chlorine, bromine, iodine, methoxy or ethoxy; arylalkyl of 7 to 12 atoms, aryl selected from phenyl or phenyl substituted by one or two groups selected from fluorine, chlorine, bromine, iodine, nitro, trifluoromethyl, $C_1$–$C_6$ alkyl, $C_1$–$C_6$ alkoxy, cyano; naphthalenyl, naphthalenyl substituted by $C_1$–$C_6$ alkyl, $C_1$–$C_6$ alkoxy, fluorine, chlorine, bromine or iodine; heteroaryl selected from pyridinyl, pyrimidinyl, pyrazinyl, indolyl, quinolinyl, isoquinolinyl, benzofuranyl, benzopyranyl, benzothiophenyl, benzimidazolyl, benzthiazolyl; cycloalkyl selected from cyclopentyl, cyclohexyl, adamantyl; or quinuclidinyl,
or a pharmaceutically acceptable salt thereof.

* * * * *